United States Patent
Swanson

(10) Patent No.: US 6,552,797 B2
(45) Date of Patent: Apr. 22, 2003

(54) FREEZING POINT MEASUREMENT WITH OCDR AND OCT TECHNOLOGY

(75) Inventor: Eric A. Swanson, Acton, MA (US)

(73) Assignee: The United States of America as represented by the Secretary of the Air Force, Washington, DC (US)

(*) Notice: Subject to any disclaimer, the term of this patent is extended or adjusted under 35 U.S.C. 154(b) by 0 days.

(21) Appl. No.: 09/907,892

(22) Filed: Jul. 13, 2001

(65) Prior Publication Data
US 2003/0011779 A1 Jan. 16, 2003

(51) Int. Cl.[7] .................................................. G01B 9/02
(52) U.S. Cl. ........................................ 356/479; 356/497
(58) Field of Search ................................. 356/497, 479

(56) References Cited

U.S. PATENT DOCUMENTS

| 5,268,741 | A | * | 12/1993 | Chou et al. .................. 356/479 |
| 5,784,352 | A | * | 7/1998 | Swanson et al. ............ 369/100 |
| 6,160,826 | A | * | 12/2000 | Swanson et al. ............ 372/102 |

* cited by examiner

Primary Examiner—Stephone B. Allen
(74) Attorney, Agent, or Firm—William G. Auton

(57) ABSTRACT

An invention pertaining to the measurement of the freezing point of substances using OCDR and OCT.technology.

1 Claim, 4 Drawing Sheets

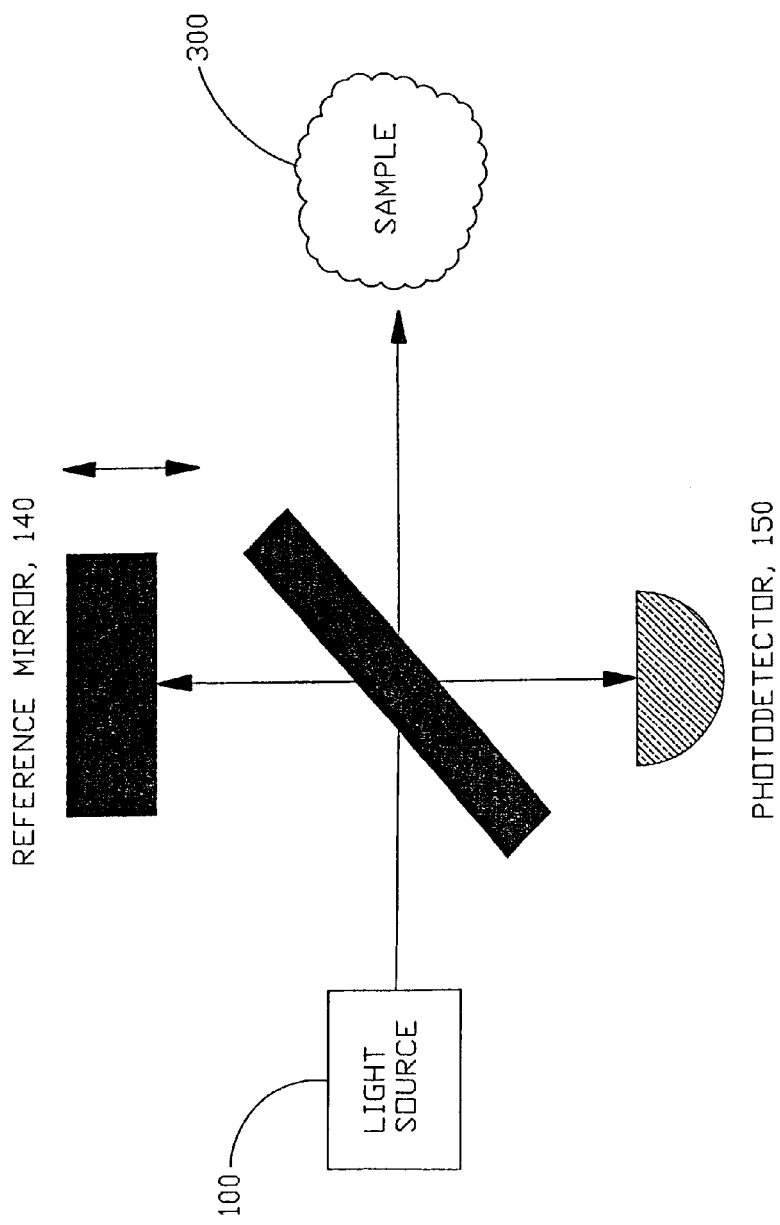
FIG. 1-A

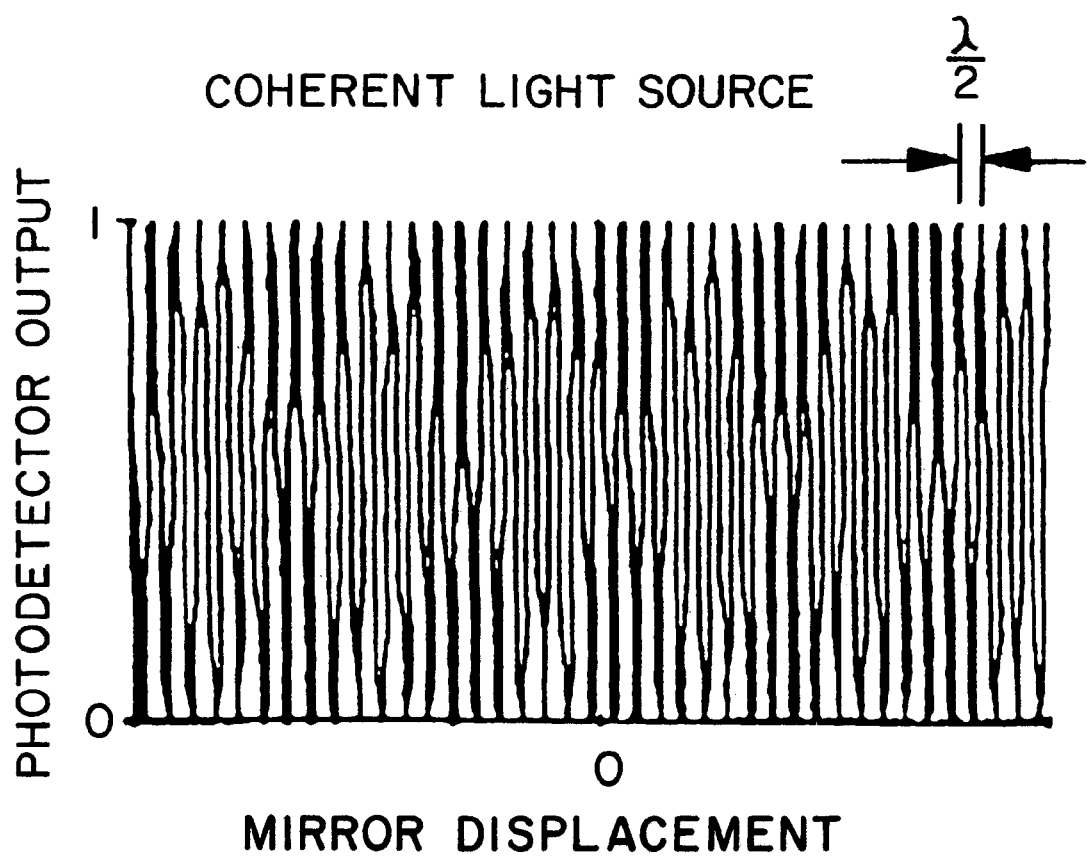
FIG. 1-B

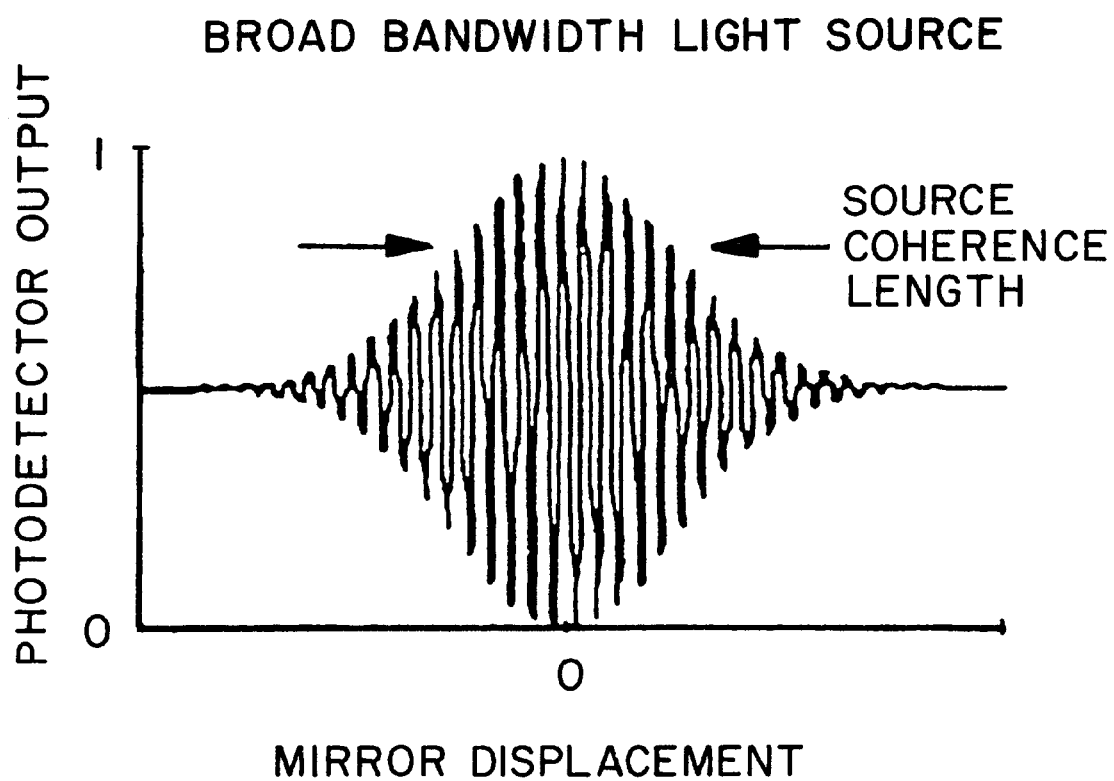
FIG. 1-C

FREEZING POINT MEASUREMENT WITH OCDR AND OCT TECHNOLOGY

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to imaging systems and more specifically to a freezing point measurement system and a process for using OCT and OCDR technology.

Optical coherence tomography (OCT) is a new imaging modality. OCT has the ability to perform high resolution, high-sensitivity, cross-sectional imaging of microstructures. The use of OCT has several significant advantages over standard optical imaging techniques and ultrasound. First, OCT can directly measure cross-sectional microstructures on a micron scale. Second, OCT can perform imaging of structures in situ and without contact. Third, imaging can be performed in real time, and, fourth, OCT technology is fiber optically based and can be interfaced with a wide range of medical, microscopic, or industrial applications.

Excellent examples of OCT applications are described in the following U.S. patents, the disclosures of which are incorporated herein by reference:

U.S. Pat. No. 6.191,862, Feb. 20, 2001, Methods and apparatus for high speed longitudinal scanning in imaging systems. Swanson, and U.S. Pat. No. 6,160,826, Dec. 12, 2000, Method and apparatus for performing optical frequency domain reflectometry, Swanson, and U.S. Pat. No. 6.157,205, Dec. 5, 2000, Grounding scheme for a high-speed data channel. Swanson, and U.S. Pat. No. 6,134,003, Oct. 17, 2000, Method and apparatus for performing optical measurements using a fiber optic imaging guidewire, catheter or endoscope, Swanson, and U.S. Pat. No. 5,777,912, Jul. 7, 1998, Linear phase finite impulse response filter with pre-addition, Leung.

As discussed in the above-cited patents, OCT is analagous to ultrasound B mode imaging, except that it uses light rather than sound and performs imaging by measuring the backscattered intensity of light from a microstructure. OCT produces one, two and three dimensional images by directing an optical beam at an object to be imaged, and measuring backscattered light as the beam is scanned across the object. The OCT image is a gray scale or false color two-dimensional representation of backscattered light intensity in a cross-sectional plane. In medical imaging, the OCT image represents the differential backscattering contrast between different tissue types on a micron scale.

There are a variety of interferometric embodiments for OCT systems. One typical implementation uses a fiber optic coupler for the Michelson interferometer. One of the arms of the interferometer is used to deliver and scan the optic beam on a sample.

In addition to OCT, other techniques can be used. For instance, in optical coherence domain reflectometry (OCDR), a longitudinally scanned reference arm and a broad bandwidth light source are used to create reflectivity profiles of a sample's optical properties. Samples of OCDR systems are described in the following U.S. Patents, the disclosures of which are incorporated herein by reference:

U.S. Pat. No. 6,160,826, Dec. 12, 2000, Method and apparatus for performing optical frequency domain reflectometry, Swanson, and U.S. Pat. No. 5,956,355, Sep. 21, 1999, Method and apparatus for performing optical measurements using a rapidly frequency-tuned laser, Swanson, and U.S. Pat. No. 5,784,352, Jul. 21, 1998, Apparatus and method for accessing data on multilayered optical media, Swanson, and U.S. Pat. No. 5,465,147, Nov. 7, 1995, Method and apparatus for acquiring images using a CCD detector array and no transverse scanner, Swanson.

There are a variety of applications where temperature at which a liquid or substance freezes (the freezing point) is an important indicator of substance properties. For instance, the freezing point of milk is a strong function of water content. A variety of industries have developed which supply instrumentation to measure freezing points. Typically they use thermo-electric coolers, super-cooling techniques, and thermisters to measure freezing point. An alternative technique to using thermisters is to use optical techniques which can resolve the phase change of the material. OCDR/OCT is one such technology. One advantage of OCDR/OCT technology is that it can spatially resolve the substance, can be used to probe very small volumes (i.e. nanoliter), and can be inexpensive, and can perform rapid measurements. This application of OCVDR/OCT technology is the focus of the present invention.

SUMMARY OF THE INVENTION

Conventional freezing point measuring apparatus typically use super-cooling techniques, thermal electric coolers, and thermisters imbedded in the specimen to measure freezing points. When sample sizes become very small or spatially resolved, optical imaging technology offers an attractive technology option. In particular, OCT and OCDR technology can measure very small volumes (—nanoliter) nondestructively. Such sizes may be too small for conventional thermister measurement approaches. It Is the focus of this invention to apply OCT/OCDR technology to freezing point measurements.

DESCRIPTION OF THE DRAWINGS

FIGS. 1a–1c are each an illustration of a complete OCDR system and process.

DESCRIPTION OF THE PREFERRED EMBODIMENT

Figure 2:
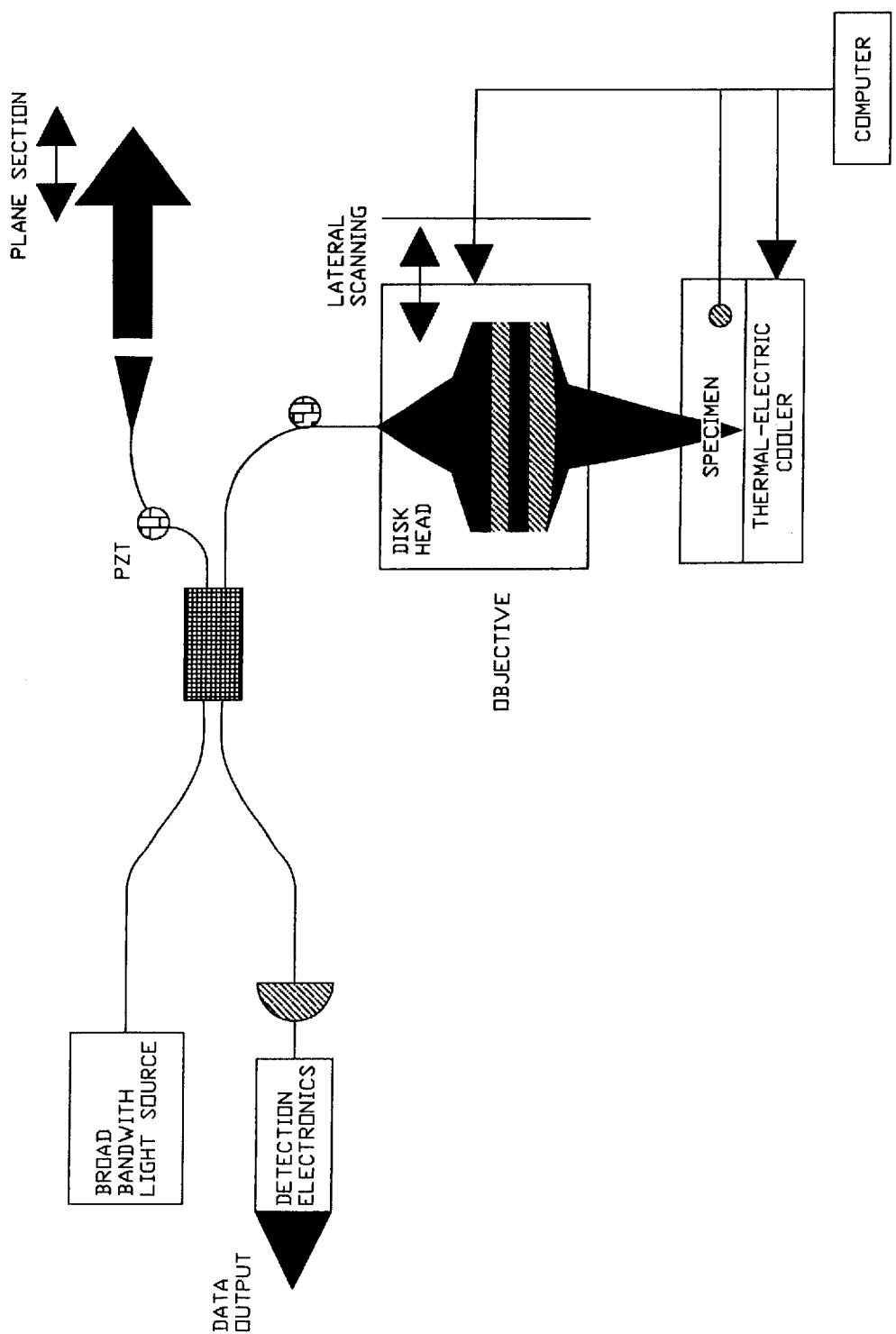
FIG. 2 is a diagram of the OCT Freezing, point measurement system.

There are a variety of embodiments of OCT/OCDR technology. This section will describe one embodiment.

OCDR measures along a single axis optical properties of a sample (index of refraction, scattering coefficient, absorption coefficient, birefringence etc.) using interferometric techniques and a short coherence length light source (i.e. light emitting diode (LED) or super-luminescent diode (SLD).

FIG. 1 shows the basic concept. In FIG. 1a, a broad bandwidth light source (100) is coupled into a Michaelson interferometer (150). One arm of the interferometer leads to the sample of interest (300), the other leads to a reference mirror (140). Reflected beams from the two arms are recombined in the beam splitter and detected on a photodetector. Due to the broad bandwidth properties of the light, only when the signal arm and the reference arm optical path length are matched to within the source coherence length is interference detected. By mechanically scanning the reference arm path length, a reflectivity profile of the samples microstructural detail is obtained. The longitudinal resolution is inversely proportional to the spectral bandwidth of the source. High longitudinal resolution (<10 $\mu$m) and large dynamic range (>$10^{12}$) can be achieved.

Suitable OCDR and OCT systems for use with this invention were described in the above-cited Swanson patents.

FIG. 2 illustrates the concept of OCDR based freezing point measurements. A liquid or other substance is placed in a container or vial. This container is optically transparent to the light source and thermally contacted to a cooler such as a thermoelectric cooler. The OCT system is under computer control. Longitudinal scanning is performed with a movable mirror such as a retro-reflector mounted on a translation stage.

Other embodiments do not require movable mirrors and use Fourier Transform Spectroscopy approaches. Lateral scanning, if necessary, can be performed by translating the sample using linear translator stages or optically using beam steering techniques, such as galvanometers. If the specimen is large a thermister can be imbedded in the specimen. If it is very small, the the thermister is attached to the container. Heterodyne detection techniques are implemented using a PZT fiber stretcher or Doppler scanning the reference arm mirror.

Initially reference measurement are performed on the specimen in its liquid state. The sample is super-cooled while images are continually acquired. The changes in the samples optical properties (absorption, scattering, birefringence, index etc.) that accompany the phase change of the sample upon freezing are detected using image processing algorithms.

While the invention has been described in its presently preferred embodiment, it is understood that the words which have been used are words of description rather than words of limitation and that changes within the purview of the appended claims may be made without departing from the scope and spirit of the invention in its broader aspects.

What is claimed is:

1. An optical coherence domain reflectometry (OCDR) freezing point measuring system which measures a freezing point from a test sample, and which comprises:

a light source which sends a broadband illuminating beam onto the test sample;

a beam splitter which splits the broadband illuminating beam into a first and second beam with the second beam reflecting off the test sample to produce a reflected second beam;

a reference mirror which reflects the first beam from the beam splitter to produce a reflected first beam; and a Michaelson interferometer photodetector system which detects the reflected second beam and the reflected first beam to output thereby a detection signal indicative of the onset of freezing in its test sample.

* * * * *